United States Patent [19]

Klauke et al.

[11] 4,329,458
[45] May 11, 1982

[54] PROCESS FOR THE PREPARATION OF 2,4,6-TRIFLUORO-1,3,5-TRIAZINE

[75] Inventors: Erich Klauke, Odenthal; Ernst Kysela, Berg.-Gladbach; Arnd Stüwe, Brunsbuettel; Alfons Dorlars, Leverkusen, all of Fed. Rep. of Germany

[73] Assignee: Bayer Aktiengesellschaft, Leverkusen, Fed. Rep. of Germany

[21] Appl. No.: 238,328

[22] Filed: Feb. 26, 1981

[30] Foreign Application Priority Data

Mar. 8, 1980 [DE] Fed. Rep. of Germany ....... 3008923

[51] Int. Cl.³ ............................................ C07D 251/28
[52] U.S. Cl. ................................................... 544/217
[58] Field of Search .......................................... 544/217

[56] References Cited

U.S. PATENT DOCUMENTS 3,008,798 11/1961 Lipscomb et al. ................. 544/217
3,641,020 2/1972 Anderson et al. ................. 544/217

*Primary Examiner*—John M. Ford
*Attorney, Agent, or Firm*—Sprung, Horn, Kramer & Woods

[57] ABSTRACT

The present invention relates to a process for the preparation of 2,4,6-trifluoro-1,3,5-triazine (TFT) from 2,4,6-trichloro-1,3,5-triazine (TCT) or from mixed chlorinated/fluorinated 1,3,5-triazines by fluorination with sodium fluoride in dipolar aprotic solvents.

The process is characterized in that TCT or mixed chlorinated/fluorinated 1,3,5-triazines or mixtures thereof are metered into a suspension of sodium fluoride in a dipolar, aprotic solvent, which is warmed to a temperature of between 120° C. and 220° C. and optionally contains a further solvent.

8 Claims, No Drawings

PROCESS FOR THE PREPARATION OF 2,4,6-TRIFLUORO-1,3,5-TRIAZINE

The present invention relates to a process for the preparation of 2,4,6-trifluoro-1,3,5-triazine (TFT) from 2,4,6-trichloro-1,3,5-triazine (TCT) or from mixed chlorinated/fluorinated 1,3,5-triazines by fluorination with sodium fluoride in dipolar aprotic solvents.

It is known that TFT can be prepared from TCT by fluorination with sodium fluoride in dipolar, aprotic solvents (C. W. Tullock and D. D. Coffman, J. Org. Chem. 25, 2016 (1960)): TCT is added to a suspension of sodium fluoride in tetramethylenesulphone and the reaction mixture is warmed in stages from 43° C. to 248° C. The TFT formed distils out of the reaction mixture. TFT is obtained in a yield of 74% of theory.

This process has considerable disadvantages with regard to industrial utilisation:

On warming the reaction mixture, when the reaction starts there is a vigorous rise in temperature which can be controlled only with difficulty in the case of large batches.

The high final reaction temperature of 248° C. necessitates expensive measures with regard to the apparatus.

It has now been found that these disadvantages in the preparation of TFT from TCT or from mixed chlorinated/fluorinated 1,3,5-triazines with sodium fluoride in a dipolar, aprotic solvent can be avoided, and at the same time more advantageous results are obtained, if TCT or mixed chlorinated/fluorinated 1,3,5-triazines or mixtures thereof are metered into a suspension of sodium fluoride in a dipolar, aprotic solvent, which is warmed to a temperature of between 120° C. and 220° C. and optionally contains a further solvent.

The reaction in the dipolar, aprotic solvent is preferably carried out between 130° and 180° C., and in particular between 140° and 160° C.

TCT can be metered in as a melt, suspension or solution. It is advantageous to meter in the TCT as a solution or suspension in one of the solvents employed in the reaction, or in a mixture of these solvents. It is likewise advantageous to use a solution or suspension of TCT in mixed chlorinated/fluorinated 1,3,5-triazines.

For an industrial process, the advantage of metering in TCT at the reaction temperature is, for example, that the jump in temperature which occurs according to the state of the art when all the reactants are introduced into the reaction vessel and are warmed together to the reaction temperature can be avoided. Surprisingly, compared with the state of the art, the yields of TFT are at least 20% higher.

TCT can be added as a melt, suspension or solution. It is advantageous to meter in the TCT as a solution or suspension in one of the solvents employed in the reaction or in a mixture of these solvents. It is likewise advantageous to use a solution or suspension of TCT in mixed chlorinated/fluorinated 1,3,5-triazines. Suitable dipolar aprotic solvents which can preferably be used for carrying out the reaction are: tetramethylenesulphone.

Suitable additives to the particular dipolar, aprotic solvent used are those solvents which are inert under the reaction conditions and have a boiling point in the range between the boiling point of TFT and the boiling point of the dipolar, aprotic solvent used (so-called "intermediate-boiling solvents"). Solvents which have boiling points in the range from 120° C. to 200° C. are preferred. Particularly preferred solvents which may be mentioned are: halogenated hydrocarbons, such as, for example, chlorobenzene or 1,2-dichlorobenzene, or alkylbenzenes, such as o-, m- or p-xylene, or mixtures thereof.

The addition of these second solvents to the reaction mixture has various advantages. An increase in the amount of product taken off and hence a higher yield (>95% of theory) is achieved; a product with a high purity (content: 99.5%) is obtained, and the reaction can be carried out at drastically reduced temperatures. The reaction is advantageously carried out between 120° C. and 200° C., using 1,2-dichlorobenzene in tetramethylenesulphone, and preferably between 130° C. and 160° C. It is remarkable that it is possible to increase the yield of TFT without adding additional sodium fluoride, whilst retaining the ratio of mols of sodium fluoride/mols of TCT of ~3.6–3.7 which has already been described in the literature. Furthermore, working up of the residue from the reaction, for example recovery of the dipolar aprotic solvent by distillation, is simplified considerably, since small residual amounts of TFT can be removed smoothly and completely with the intermediate-boiling solvent (the TFT-containing intermediate-boiling solvent can be re-used in subsequent batches, as can the dipolar, aprotic solvent recovered). In addition, ecologically acceptable metal salts, the diposal of which presents no problems, are obtained.

It is to be described as decidedly surprising that the end product 2,4,6-trifluoro-triazine is obtained in a high purity and without a significant content of the by-products 2,4-difluoro-6-chloro-1,3,5-triazine and 2-fluoro-4,6-dichloro-1,3,5-triazine on adding the second solvent, which, as a so-called intermediate-boiling solvent, is known to have a function as an entraining agent.

The second solvent employed as an intermediate-boiling solvent can be used in an amount of 0.05–0.6 mol, relative to the dipolar aprotic solvent employed, but preferably in amounts of 0.2–0.4 mol, such as, for example, in the case of 1,2-dichlorobenzene/tetramethylenesulphone. In general, TCT is reacted with NaF in a molar ratio of 1:3 to 1:5, preferably 1:3.3 to 1:4.

TFT is an intermediate product which can be used in many ways and is suitable, for example, for the preparation of reactive dyestuffs and herbicides. The process according to the invention may be illustrated with the aid of the following examples.

EXAMPLE 1

454 g (10.8 mols) of NaF and 520 g of tetramethylenesulphone are initially introduced into a reactor with paddles and are warmed to 160° C., whilst stirring. A hot solution, at 140° C., of 555 g (3 mols) of TCT in 300 g of tetramethylenesulphone is then metered in over a period of one hour. After about 30–50% has been introduced, TFT starts to distill off. After the end of the addition, the temperature is increased to 190° C. in the course of one hour and the reactor is gradually evacuated to about 50 mbar, whilst maintaining this temperature. 360 g of TFT (89% of theory) are obtained.

EXAMPLE 2

900 g of NaF (21.5 mols) in 150 g of tetramethylenesulphone (dried by distillation) and 300 g of 1,2-dichlorobenzene are initially introduced into a 3 l reactor with paddles. A suspension of 1,107 g of TCT (6 mols) in 924 g of tetramethylenesulphone (suspension temperature: 30°–35° C.) is metered into the reactor with paddles at an internal temperature of about 140°–150° C. in the course of 60–75 minutes.

When the amount of suspension metered in is 800–820 g, TFT starts to distil off over a column under normal pressure. When metering in of the suspension has ended, 350–400 g of TFT have distilled off.

The temperature is then increased to 180°–190° C. in the course of 40–60 minutes. Under these conditions, 693 g of TFT ($\triangleq$ 85.2% of theory, relative to the TCT employed) are obtained.

The pressure in the reactor is then reduced to 450 mbar, whereupon a further 79 g of TFT ($\triangleq$ 10% of theory) distil off. 295 g of 1,2-dichlorobenzene are distilled off, as the intermediate-boiling solvent, by increasing the vacuum further to 100 mbar.

1,000 g of tetramethylenesulphone are recovered on further reduction of the pressure in the reactor.

A light-coloured, pulverulent, odourless salt residue remains in the reactor with paddles and can easily be discharged from the reactor with paddles. Yields: TFT: 96.5% of theory, relative to TCT reacted (content: 99.5%); 1,2-dichlorobenzene: 98.3%, relative to the amount employed (content: 97.9%); and tetramethylenesulphone: 93.1%, relative to the amount employed (content: 99%).

EXAMPLE 3

The reaction is carried out analogously to Example 2, but instead of the TCT suspension, a mixture of 8.4% of TFT, 20.3% of difluorochlorotriazine, 33.9% of dichlorofluorotriazine and 36.1% of TCT is metered in (the tetramethylenesulphone required for the suspension in Example 2 is initially introduced into the reactor with paddles). 375–390 g of TFT ($\triangleq$ 92–96% of theory) are obtained.

The mixture of TFT, difluorochlorotriazine, dichlorofluorotriazine and TCT employed as the reactant according to Example 3 can be obtained as follows, in accordance with Example 1–3 of DE-OS (German Published No.) 2,702,625:

200 g of cyanuric chloride and 100 g of cyanuric fluoride are brought together with 3 g of active charcoal at 180° C. for 30 minutes. A mixture consisting of 8.4% of TFT, 20.3% of difluorochlorotriazine, 33.9% of dichlorofluorotriazine and 36.1% of TCT is then obtained.

We claim:

1. Process for the preparation of 2,4,6-trifluoro-1,3,5-triazine (TFT) from 2,4,6-trichloro-1,3,5-triazine (TCT) or from mixed chlorinated/fluorinated 1,3,5-triazines by fluorination with NaF in a dipolar, aprotic solvent, characterised in that TCT is metered into a suspension warmed to 120° C. to 220° C., of NaF in a dipolar, aprotic solvent, which optionally contains a further solvent.

2. Process according to claim 1, characterised in that the dipolar, aprotic solvent is tetramethylenesulphone.

3. Process according to claim 1, characterised in that a further solvent which is inert and which has a boiling point between the boiling point of TFT and the boiling point of the dipolar, aprotic solvent is added to the dipolar, aprotic solvent.

4. Process according to claim 1, characterised in that TCT is employed as a melt or as a solution or suspension in one of the solvents employed in the reaction or in a mixture of these solvents.

5. Process according to claim 1, characterised in that TCT is metered in as a mixture with or solution in mixed chlorinated/fluorinated 1,3,5-triazines, or mixed chlorinated/fluorinated 1,3,5-triazines are used.

6. Process according to claim 1, characterised in that the further solvents used are preferably those which have boiling points between 120°–200° C. and which are halogenated hydrocarbons or alkylbenzenes.

7. Process according to claim 6, characterised in that the halogenated hydrocarbon employed as the further solvent is chlorobenzene or 1,2-dichlorobenzene and the alkylbenzenes are o-, m- or p-xylene, or mixtures thereof.

8. Process according to claim 3, characterised in that the second solvent is employed in an amount of 0.05–0.6 mol, relative to the dipolar, aprotic solvent employed.

* * * * *